United States Patent
Iwahori et al.

(10) Patent No.: US 9,192,708 B2
(45) Date of Patent: Nov. 24, 2015

(54) DIALYSATE EXTRACTION APPARATUS

(71) Applicant: Nikkiso Company Limited, Tokyo (JP)

(72) Inventors: Tadashi Iwahori, Shizuoka (JP);
Masahiro Takahashi, Shizuoka (JP);
Kazumi Yokoyama, Shizuoka (JP);
Hachiro Edamura, Shizuoka (JP);
Yusuke Nakano, Shizuoka (JP);
Fumihiko Ishizaki, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 0 days.

(21) Appl. No.: 14/197,329

(22) Filed: Mar. 5, 2014

(65) Prior Publication Data

US 2014/0183114 A1    Jul. 3, 2014

Related U.S. Application Data

(63) Continuation of application No. PCT/JP2012/072976, filed on Sep. 7, 2012.

(30) Foreign Application Priority Data

Sep. 9, 2011   (JP) .................................. 2011-196869

(51) Int. Cl.
*F16K 49/00*   (2006.01)
*A61M 39/16*   (2006.01)
(Continued)

(52) U.S. Cl.
CPC ............. *A61M 1/168* (2013.01); *A61M 1/1619* (2014.02); *A61M 1/1686* (2013.01); *A61M 39/10* (2013.01);
(Continued)

(58) Field of Classification Search
CPC ... A61M 1/166; A61M 1/168; A61M 1/1664; A61M 1/1686; A61M 1/1619; A61M 39/20; A61M 2039/1088; A61M 2039/167; B01D 61/24; B01D 61/28; B01D 61/30; F16K 49/002

USPC ........ 422/537, 118; 215/28, 29; 210/646, 648
See application file for complete search history.

(56) References Cited

U.S. PATENT DOCUMENTS

2008/0053530 A1*   3/2008   Knight et al. ..................... 432/1

FOREIGN PATENT DOCUMENTS

JP   H03-73162 A    3/1991
JP   2004-313522 A   11/2004
(Continued)

OTHER PUBLICATIONS

Translation of International Search Report, Application No. PCT/JP2012/072976, dated Dec. 4, 2012.
(Continued)

*Primary Examiner* — Krishnan S Menon
*Assistant Examiner* — Waqaas Ali
(74) *Attorney, Agent, or Firm* — The Dobrusin Law Firm, P.C.

(57) ABSTRACT

To provide a dialysate extraction apparatus which can automate disinfecting work for a collection port or a sealing device of an opening/closing device and can reliably and easily clean the collection port or the sealing device of the opening/closing device. A dialysate extraction apparatus includes a dialysate extraction device that has an introduction port and a discharge port which are connected to a flow route of a liquid and can circulate the liquid and that has a collection port which can collect the circulated liquid; a cap that is attachable to and detachable from the collection port of the dialysate extraction device and can open and close the collection port; a sealing device that is attached to the cap and seals the collection port in a state where the cap is attached to the collection port of the dialysate extraction device; and a heating device that can heat the sealing device of the cap.

20 Claims, 12 Drawing Sheets

(51) Int. Cl.
  *A61M 1/14*   (2006.01)
  *A61M 1/16*   (2006.01)
  *A61M 39/10*  (2006.01)
  *A61M 39/20*  (2006.01)
  *F24H 1/00*   (2006.01)
  *B01D 35/147* (2006.01)
  *B01D 35/153* (2006.01)

(52) U.S. Cl.
  CPC .............. *A61M 39/20* (2013.01); *F16K 49/002* (2013.01); *A61M 2039/1088* (2013.01); *A61M 2039/167* (2013.01); *B01D 35/147* (2013.01); *B01D 35/153* (2013.01); *F24H 1/00* (2013.01)

(56) References Cited

FOREIGN PATENT DOCUMENTS

| | | | |
|---|---|---|---|
| JP | 2009-207706 A | | 9/2009 |
| JP | 2009207706 A | * | 9/2009 |
| JP | 2011-161060 A | | 8/2011 |

OTHER PUBLICATIONS

European Search Report for Application No. 12830761.8 dated Apr. 10, 2015.

* cited by examiner

DIALYSATE EXTRACTION APPARATUS

FIELD

The present invention relates to a dialysate extraction apparatus that includes a dialysate extraction device having an introduction port and a discharge port which are connected to a flow route of a liquid and can circulate the liquid and having a collection port which can collect the circulated liquid; an opening/closing device which is attachable to and detachable from the collection port of the dialysate extraction device and can open and close the collection port; and a sealing device which is attached to the opening/closing device and seals the collection port in a state where the opening/closing device is attached to the collection port of the dialysate extraction device.

BACKGROUND

In recent years, in a dialysis apparatus as a blood purification apparatus, a technology has been proposed in which priming, returning of blood and substitution (emergency fluid infusion) are performed by using a dialysate to be supplied to a dialyzer during dialysis treatment (in particular, online HDF or online HF), or a technology has been proposed in which the dialysate is used as a substitution solution for the online HDF or online HF treatment. For example, PTL 1 discloses a dialysis apparatus including a substitution line where one end is connected to a dialysate extraction port (collection port) formed in a predetermined section of a dialysate introduction line and the other end is connected to a blood circuit (arterial blood circuit or venous blood circuit): and a substitution pump which is arranged in the substitution line. In order for such a dialysis apparatus to perform the priming, the returning of blood or the substitution (emergency fluid infusion), the substitution pump is rotated to supply the dialysate in the dialysate introduction line to the blood circuit (arterial blood circuit or venous blood circuit).

In general, a cap (opening/closing device) is attachable to and detachable from the dialysate extraction port, and the substitution line is connected by detaching the cap and when the substitution line is not connected, the dialysate flowing in the dialysate introduction line is not caused to leak out by attaching the cap. For example, in order to clean and disinfect a pipe for circulating the dialysate, such as the dialysate introduction line and the dialysate discharge line, cleaning water or disinfecting solution is circulated in the pipe in a state where the cap is attached to the collection port. In this manner, the cleaning water or the disinfecting solution is prevented from leaking out. An example may be found in PTL 1: Japanese Unexamined Patent Application Publication No. 2004-313522.

SUMMARY

However, in the dialysate extraction apparatus in the related art, when inserting a syringe or a connecting line to the collection port, there is a possibility that bacteria may cling thereto. Thus, in order to perform cleaning, an operator such as a health care worker carries out disinfecting work using alcohol on all occasions. In addition, even for the cap which is attachable to and detachable from the collection port (in particular, sealing device for sealing the collection port), similar to the collection port, the operator such as the health care worker carries out the disinfecting work using the alcohol on all occasions, thereby causing the disinfecting work to require much time and labor.

The present invention is made in view of the above-described circumstances, and aims to provide a dialysate extraction apparatus which can automate disinfecting work for a collection port or a sealing device of an opening/closing device and can reliably and easily clean the collection port or the sealing device of the opening/closing device.

According to the invention described in the teachings herein, there is provided a dialysate extraction apparatus including a dialysate extraction device that has an introduction port and a discharge port which are connected to a flow route of a liquid and can circulate the liquid and that has a collection port which can collect the circulated liquid: an opening/closing device that is attachable to and detachable from the collection port of the dialysate extraction device and can open and close the collection port: a sealing device that is attached to the opening/closing device and seals the collection port in a state where the opening/closing device is attached to the collection port of the dialysate extraction device; and a heating device that can heat the sealing device of the opening/closing device.

According to the invention described in the teachings herein, in the dialysate extraction apparatus described in the teachings herein, the heating device is fixed to the opening/closing device.

According to the invention described in the teachings herein, in the dialysate extraction apparatus described in the teachings herein, the heating device can heat and disinfect the collection port via the sealing device in a state where the opening/closing device is attached to the collection port of the dialysate extraction device.

According to the invention described in the teachings herein, the dialysate extraction apparatus described in the teachings herein includes a placement device that places the opening/closing device detached from the collection port of the dialysate extraction device. The heating device is attached to the placement device.

According to the invention described in the teachings herein, the dialysate extraction apparatus described in the teachings herein includes a holding device that holds the opening/closing device and can switch between a state where the opening/closing device is attached to the collection port of the dialysate extraction device and a state where the opening/closing device is detached from the collection port.

According to the invention described in the teachings herein, in the dialysate extraction apparatus described in the teachings herein, the heating device includes a semiconductor heater which can perform heating by means of energizing and can be held at a setting temperature.

According to the invention described in the teachings herein, a blood purification apparatus includes the dialysate extraction apparatus described in the teachings herein.

According to the invention described in the teachings herein, the apparatus is provided with the heating device that can heat the sealing device of the opening/closing device. Therefore, it is possible to automate disinfecting work for the collection port or the sealing device of the opening/closing device and to reliably and easily clean the collection port or the sealing device of the opening/closing device.

According to the invention described in the teachings herein, the heating device is fixed to the opening/closing device. Therefore, it is possible to heat and disinfect the sealing device either in a state where the opening/closing device is attached to the collection port or in a state where the opening/closing device is detached from the collection port.

According to the invention described in the teachings herein, the heating device can heat and disinfect the collection port via the sealing device in a state where the opening/ closing device is attached to the collection port of the dialysate extraction device. Therefore, it is possible to reliably disinfect the collection port in a closed state.

According to the invention described in the teachings herein, the apparatus is provided with the placement device that places the opening/closing device detached from the collection port of the dialysate extraction device, and the heating device is attached to the placement device. Therefore, it is possible to avoid loss of the opening/closing device detached from the collection port by using the placement device, and it is possible to achieve heat disinfection for the placed opening/closing device.

According to the invention described in the teachings herein, the apparatus is provided with the holding device that holds the opening/closing device and can switch between a state where the opening/closing device is attached to the collection port of the dialysate extraction device and a state where the opening/closing device is detached from the collection port. Therefore, it is possible to easily and reliably attach or detach the opening/closing device to or from the collection port.

According to the invention described in the teachings herein, the heating device includes a semiconductor heater which can perform heating by means of energizing and can be held at a setting temperature. Therefore, it is possible to eliminate a need for a separate device such as a thermistor for keeping the temperature constant, and thus, it is possible to simplify a configuration of the apparatus.

According to the invention described in the teachings herein, it is possible to provide the blood purification apparatus including the dialysate extraction apparatus which can automate the disinfecting work for the collection port or the sealing device of the opening/closing device and can reliably and easily clean the collection port or the sealing device of the opening/closing device.

DETAILED DESCRIPTION

Hereinafter, embodiments of the present invention will be described in detail with reference to the drawings.

Figure 1:
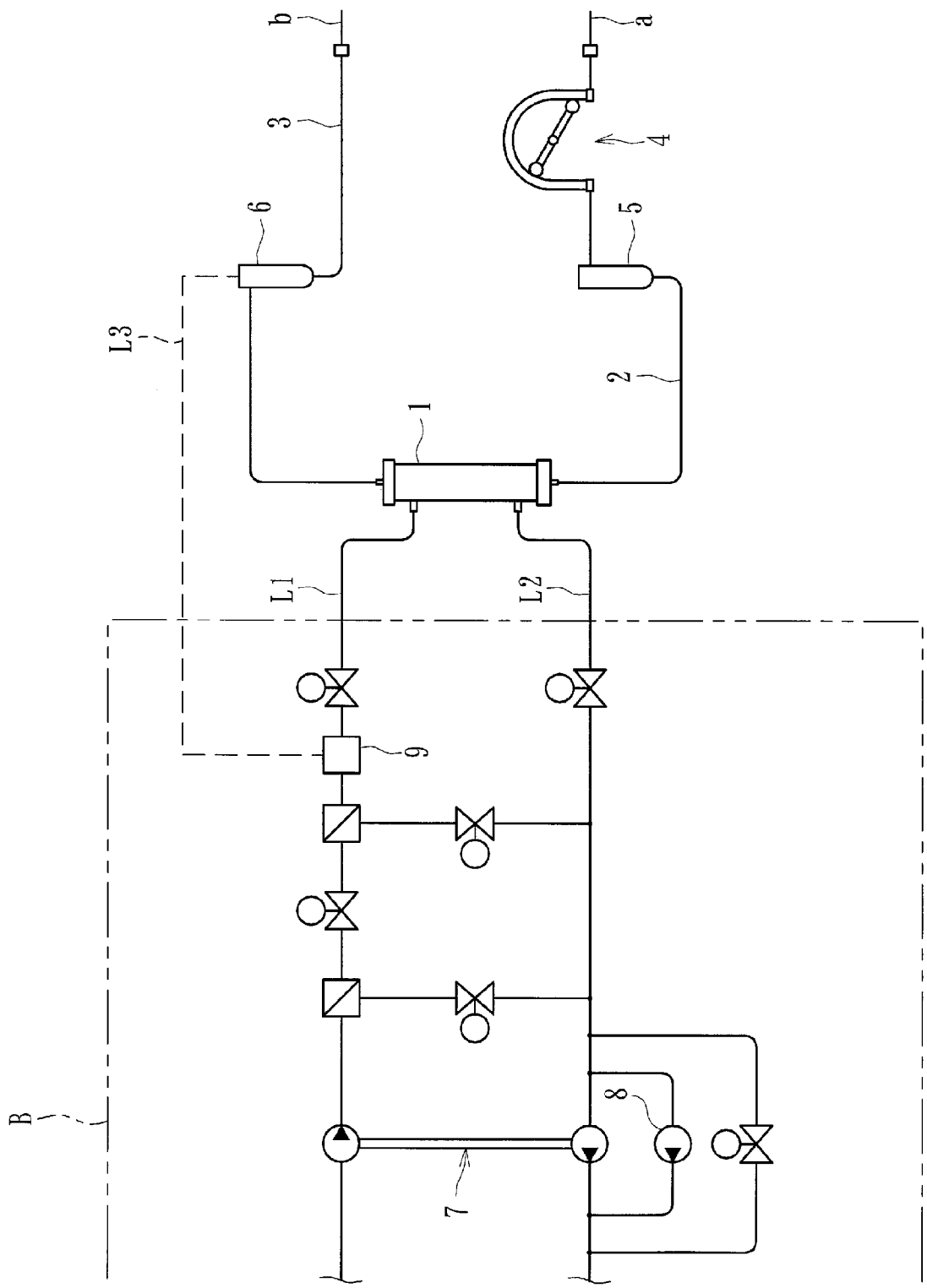
FIG. 1 is a schematic view illustrating a blood purification apparatus which employs a dialysate extraction apparatus of the present invention.

A dialysate extraction apparatus according to a first embodiment is arranged in a blood purification apparatus used in blood purification treatment (hemodialysis treatment) and can collect dialysate. As illustrated in FIG. 1, the employed blood purification apparatus is mainly configured to include a blood circuit in which an arterial blood circuit 2 and a venous blood circuit 3 are connected to a dialyzer 1 (blood purifier); and a dialysis device B which has a dialysate introduction line L1 and a dialysate discharge line L2.

The dialyzer 1 is to purify blood and is connected to the arterial blood circuit 2 and the venous blood circuit 3 respectively which configure the blood circuit. The dialyzer 1 is connected to the dialysate introduction line L1 and the dialysate discharge line L2 respectively. Patient's blood collected through an arterial puncture needle a is extracorporeally circulated in the blood circuit, and the dialyzer 1 performs blood purification and ultrafiltration to return the blood to the patient through a venous puncture needle b. A reference numeral 4 illustrates a blood pump which is a peristaltic pump. Reference numerals 5 and 6 illustrate air trap chambers.

In addition, a duplex pump 7 which supplies the dialyzer 1 with the dialysate prepared to have predetermined concentration and discharges the dialysate from the dialyzer 1 is connected to the dialysate introduction line L1 and the dialysate discharge line L2. Further, a plurality of bypass lines and electromagnetic valves are arranged in desired positions inside the dialysis device B. An ultrafiltration pump 8 is connected to the bypass line which bypasses the duplex pump 7.

Then, in order to disinfect or clean a pipe inside the dialysis device B, tips of the dialysate introduction line L1 and the dialysate discharge line L2 are detached from the dialyzer 1, and the pipe is short-circuited by connecting the tips to each other using a coupler for example. Thereafter, disinfecting solution (hot water or disinfecting chemical) or cleaning water (clean water) is introduced from outside of the dialysis device B (for example, dialysate supplying device), and a liquid (dialysate or the like) inside the pipe in the dialysis device B is substituted. For example, the disinfecting solution may be introduced into the pipe from the inside of a tank for substitution by a flow route branched from the dialysate discharge line 12 and by inserting the tip to the tank containing the disinfecting solution.

Figure 2:
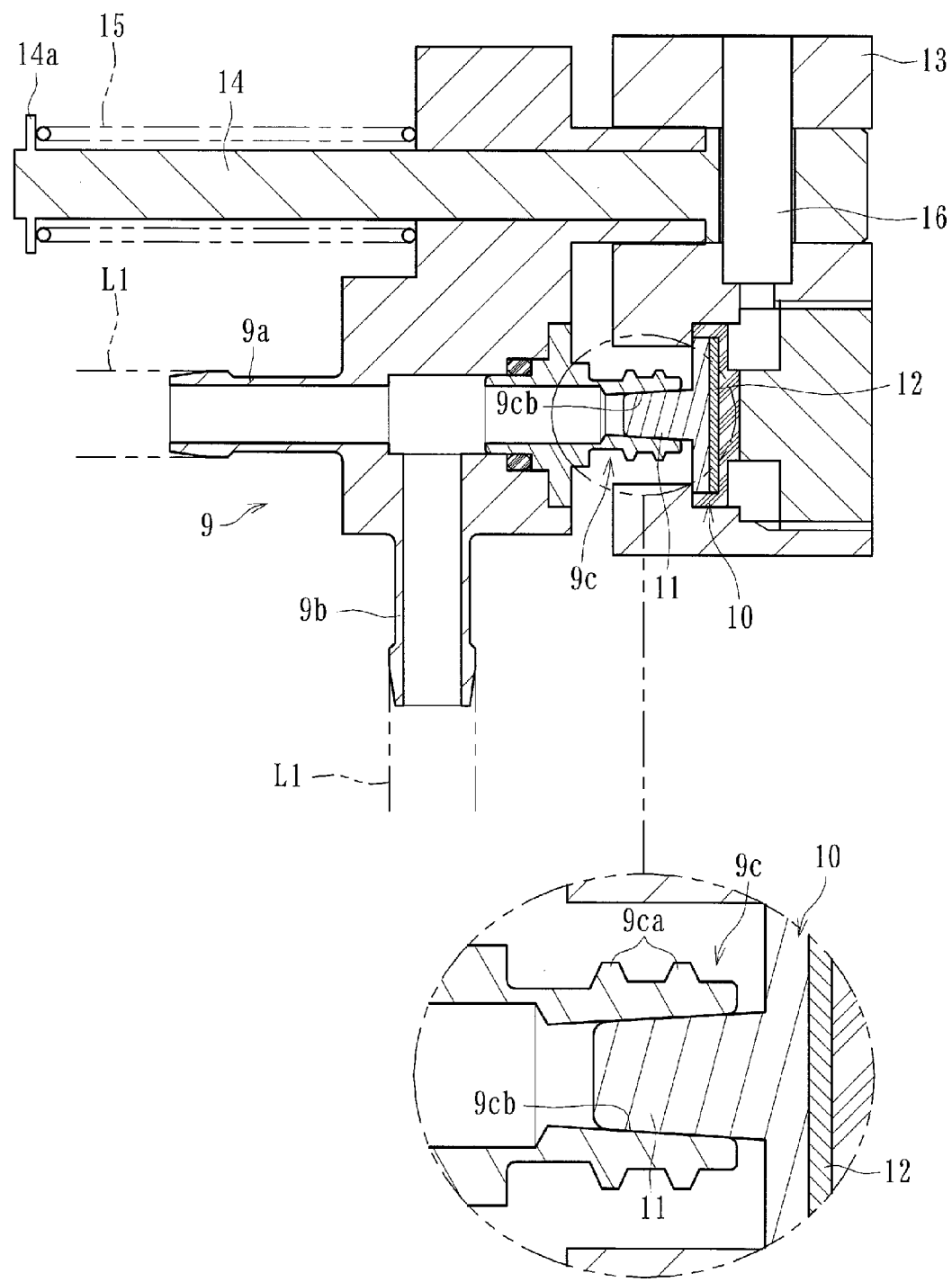
FIG. 2 is a schematic cross-sectional view illustrating a dialysate extraction apparatus (state where an opening/closing device is attached to a collection port) according to a first embodiment of the present invention.
Figure 3:
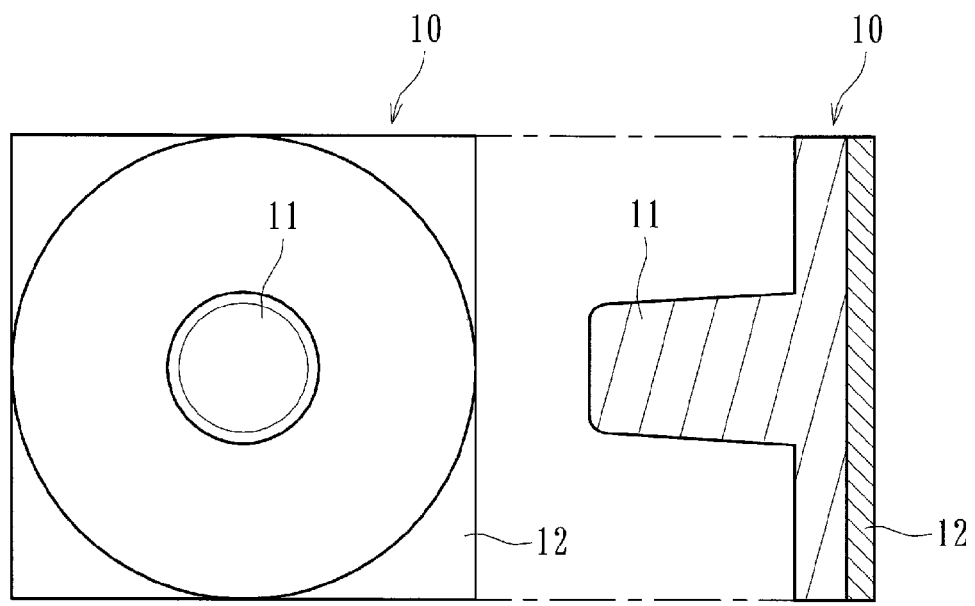
FIG. 3 is a front view and a side view illustrating a cap (opening/closing device) in the dialysate extraction apparatus.
Figure 4:
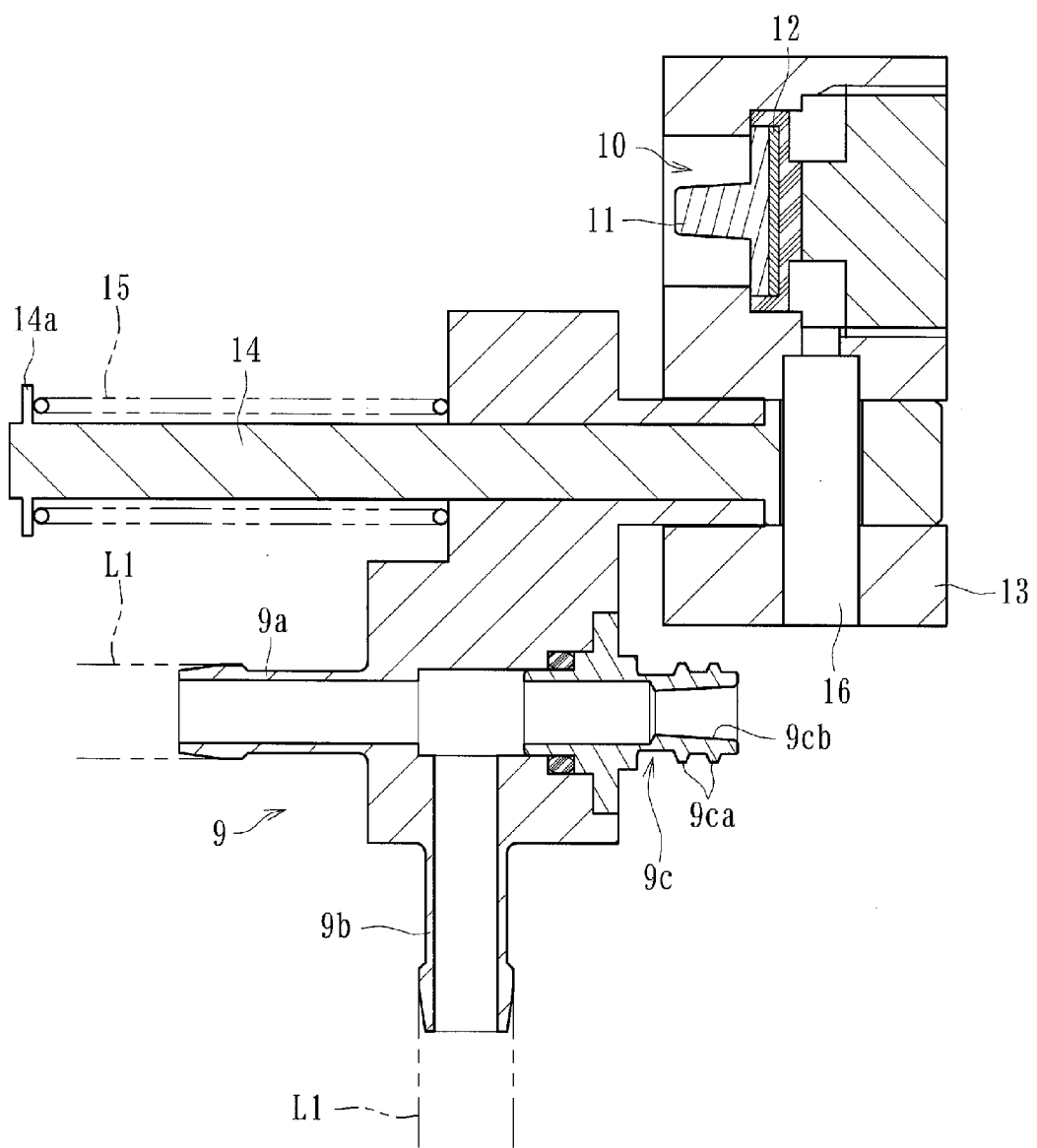
FIG. 4 is a schematic cross-sectional view illustrating a dialysate extraction device (state where the opening/closing device is detached) of the dialysate extraction apparatus.

Here, the dialysate extraction apparatus according to the first embodiment of the present invention is connected to the dialysate introduction line L1. As illustrated in FIGS. 2 to 4, the dialysate extraction apparatus according to the present embodiment includes an introduction port 9*a* and a discharge port 9*b* which are connected to the dialysate introduction line L1 (flow route of a liquid) and which can circulate the liquid (dialysate); a dialysate extraction device 9 having a collection port 9*c* which can collect the circulated liquid; a cap 10 serving as an opening/closing device; a sealing device 11; and a heating device 12.

More specifically, in the dialysate extraction device 9, the dialysate introduction line L1 is connected to the introduction port 9*a* and the discharge port 9*b* respectively, and the dialysate can be internally circulated. The flow route (flow route through which the dialysate flows from the introduction port 9*a* to the discharge port 9*b* ) is extended in an L-shape bent by approximately 90 degrees. The collection port 9*c* is formed to be positioned on a substantially identical straight line with respect to the introduction port 9*a* . In the present embodiment, a portion having the collection port 9*c* is formed to have a member separate from that of a portion having the introduction port 9*a* and the discharge port 9*b* . These portions are configured to be connected to each other via a sealing member, but may be an integrated component.

Furthermore, a syringe (not illustrated) or a connecting device such as a connecting line L3 (substitution line whose tip is connected to a predetermined portion of the blood circuit) is connected to the collection port 9*c* in a state where the cap 10 (opening/closing device) is detached from the collection port 9*c* , on an outer surface of which a male threaded portion 9*ca* is formed. The male threaded portion 9*ca* is formed to mesh with a lock ring formed on a base end of the connecting line L3, and can be fixed to the connecting line L3 by screwing the lock ring.

The connecting line L3 according to the present embodiment is connected to an air trap chamber 5 connected to the arterial blood circuit 2 or to an air trap chamber 6 connected to the venous blood circuit 3 for example, and can supply the dialysate in the dialysate introduction line L1 to the arterial blood circuit 2 or the venous blood circuit 3. In this manner, it is possible to perform priming, substitution or returning of blood by using the dialysate. Alternatively, it is possible to use the dialysate as a substitution solution for online HDF or online HF treatment.

The cap 10 as the opening/closing device is attachable to and detachable from the collection port 9*c* of the dialysate extraction device 9, capable of opening and closing the collection port 9*c* , and is adapted to have the sealing device 11 and the heating device 12. Among them, the sealing device 11 is attached to the cap 10, seals the collection port 9*c* in a state where the cap 10 is attached to the collection port 9*c* of the dialysate extraction device 9, and can seal the collection port 9*c* by being inserted through a tip opening of the collection port 9*c*.

The heating device 12 can heat the sealing device 11 of the cap 10, and is adapted to have a semiconductor heater arranged so that a heating unit thereof is in close contact with the sealing device 11 in the present embodiment. The semiconductor heater is configured to have a semiconductor which can perform self-controlling so that heating can be performed by means of energizing and can be held at a setting temperature. The semiconductor heater has characteristics of bendability, excellent shock-resistance and low power consumption. The heating device 12 is connected to a wire (not illustrated), and can be energized at any desired time.

If the heating device 12 is energized and heated, it is possible to heat the sealing device 11. The heat is transferred to the collection port 9*c* of the dialysate extraction device 9 via the sealing device 11, and thus, it is possible to heat a portion for sealing 9*cb* of the collection port 9*c* (inner peripheral surface of the tip side of the collection port 9*c* ). That is, the heating device 12 can heat and disinfect both of the sealing device 11 and the portion for sealing 9*cb* of the collection port 9*c* , respectively.

In order to obtain a sufficient disinfecting effect, it is preferable that the setting temperature of the heating device 12 be 65° C. or higher for example, or more preferably 80° C. or higher. In addition, the energizing for the heating device 12 may be performed either in a state where the cap 10 is attached to the collection port 9*c* (for example, during a period when the treatment is not performed until subsequent treatment is performed) or in a state where the cap 10 is detached from the collection port 9*c* . The energizing may be performed either by repeating on-off operations for a constant period of time or by the on-off operations using a program.

However, in the present embodiment, the apparatus is provided with a holding device 13 which holds the cap 10 and can switch between a state where the cap 10 is attached to the collection port 9*c* of the dialysate extraction device 9 (refer to FIG. 2) and a state where the cap 10 is detached from the collection port 9*c* (refer to FIG. 4). As illustrated in FIG. 2, the holding device 13 is configured to have a shaft member 14, a spring 15 and a shaft member 16, and is rotatable about a center of the shaft member 14. In addition, a spring bracket 14*a* is formed in the base end of the shaft member 14, and the spring 15 is interposed between the spring bracket 14*a* and the dialysate extraction device 9. In this manner, the holding device 13 is always biased in the leftward direction in FIG. 2 by the biasing force of the spring 15.

In a state where the cap 10 covers the collection port 9*c* (refer to FIG. 2), the cap 10 is pressed against the collection port 9*c* by the biasing force of the spring 15, thereby holding a closed state. In addition, if the holding device 13 together with the cap 10 is moved (moved in the rightward direction in FIG. 2) against the biasing force of the spring 15, the cap 10 is left in a state separated away from the collection port 9*c* , and the cap 10 is rotated about the center of the shaft member 14, it is possible to leave the collection port 9*c* in an opened state as illustrated in FIG. 4. In this manner, it is possible to connect the syringe or the connecting device such as the connecting line L3 to the collection port 9*c*.

According to the present embodiment, the apparatus is provided with the heating device 12 which can heat the sealing device 11 of the cap 10. Therefore, it is possible to automate the disinfecting work for the collection port 9*c* or the sealing device 11 of the cap 10. It is possible to reliably and easily clean the collection port 9*c* or the sealing device 11 of the cap 10. In addition, according to the present embodiment, the heating device 12 is fixed to the cap 10. Therefore, it is possible to heat and disinfect the sealing device 11 either in a state where the cap 10 is attached to the collection port 9*c* or in a state where the cap 10 is detached from the collection port 9*c*.

Further, according to the present embodiment, in a state where the cap 10 is attached to the collection port 9*c* of the dialysate extraction device 9, the heating device 12 can heat and disinfect the collection port 9*c* via the sealing device 11. Therefore, it is possible to reliably disinfect the collection port 9*c* in a closed state. Furthermore, the heating device 12 according to the present embodiment is adapted to have the semiconductor heater which can perform heating by means of energizing and can be held at the setting temperature. Therefore, it is possible to eliminate a need for a separate device such as a thermistor for keeping the temperature constant, and thus, it is possible to simplify a configuration of the apparatus.

In addition, the cap 10 is held by the holding device 13. Therefore, it is possible to firmly and reliably seal the collection port 9c by using the cap 10, and it is possible to avoid loss of the cap 10 when the collection port 9c is left in an opened state. In addition, if there is provided a detection device for detecting a direction of the holding device 13 (rotating position about the center of the shaft member 14), it is possible to detect whether the collection port 9c is in an opened state or in a closed state.

Next, a dialysate extraction apparatus according to a second embodiment of the present invention will be described.

Figure 5:
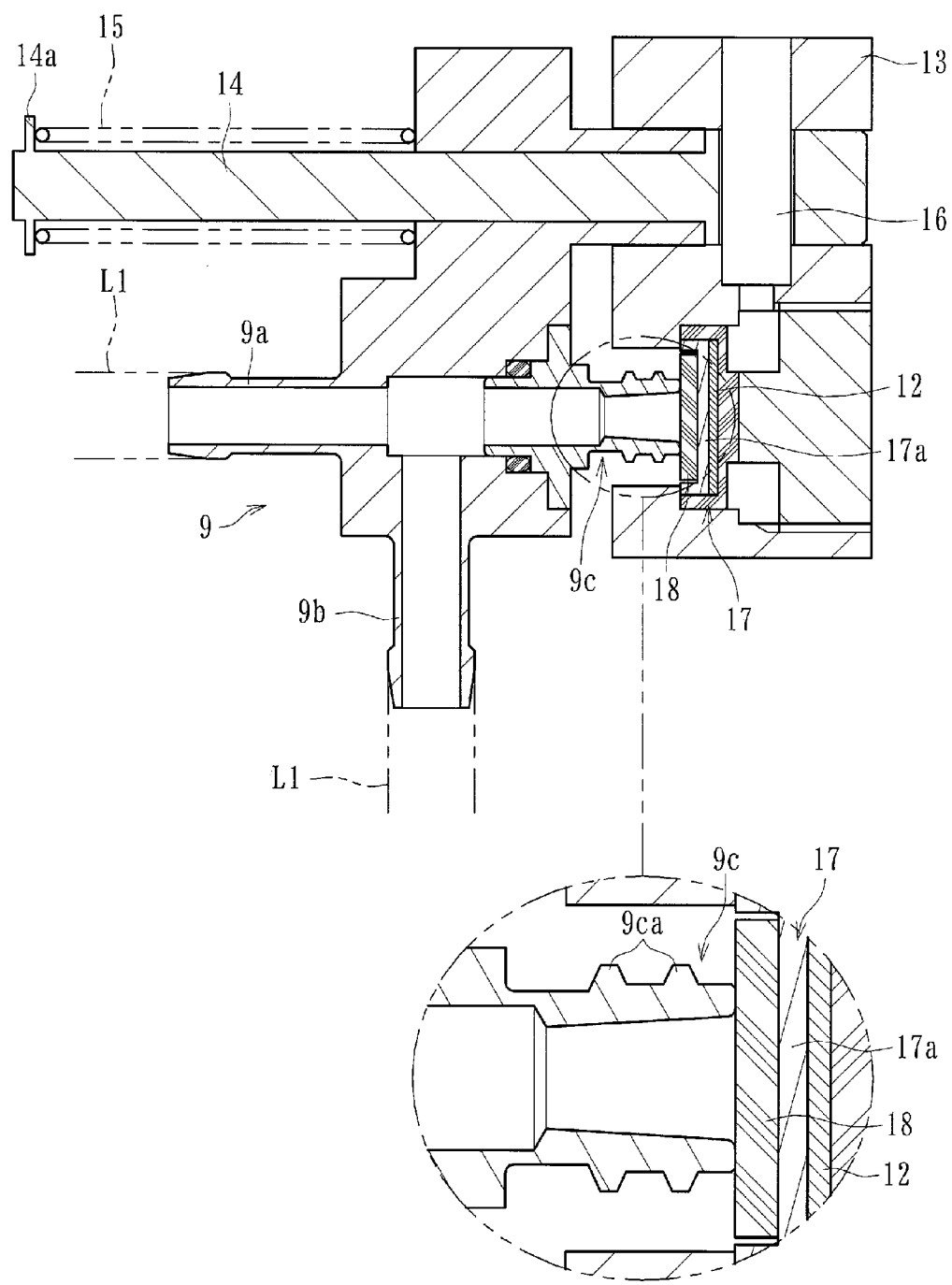
FIG. 5 is a schematic cross-sectional view illustrating a dialysate extraction apparatus (state where an opening/closing device is attached to a collection port) according to a second embodiment of the present invention.
Figure 6:
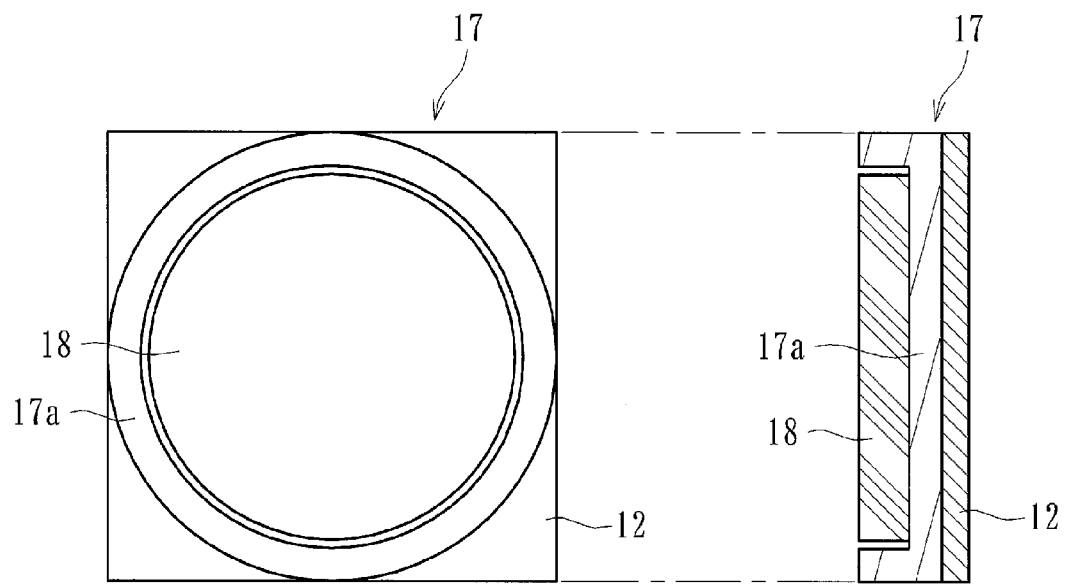
FIG. 6 is a front view and a side view illustrating a cap (opening/closing device) in the dialysate extraction apparatus.
Figure 7:
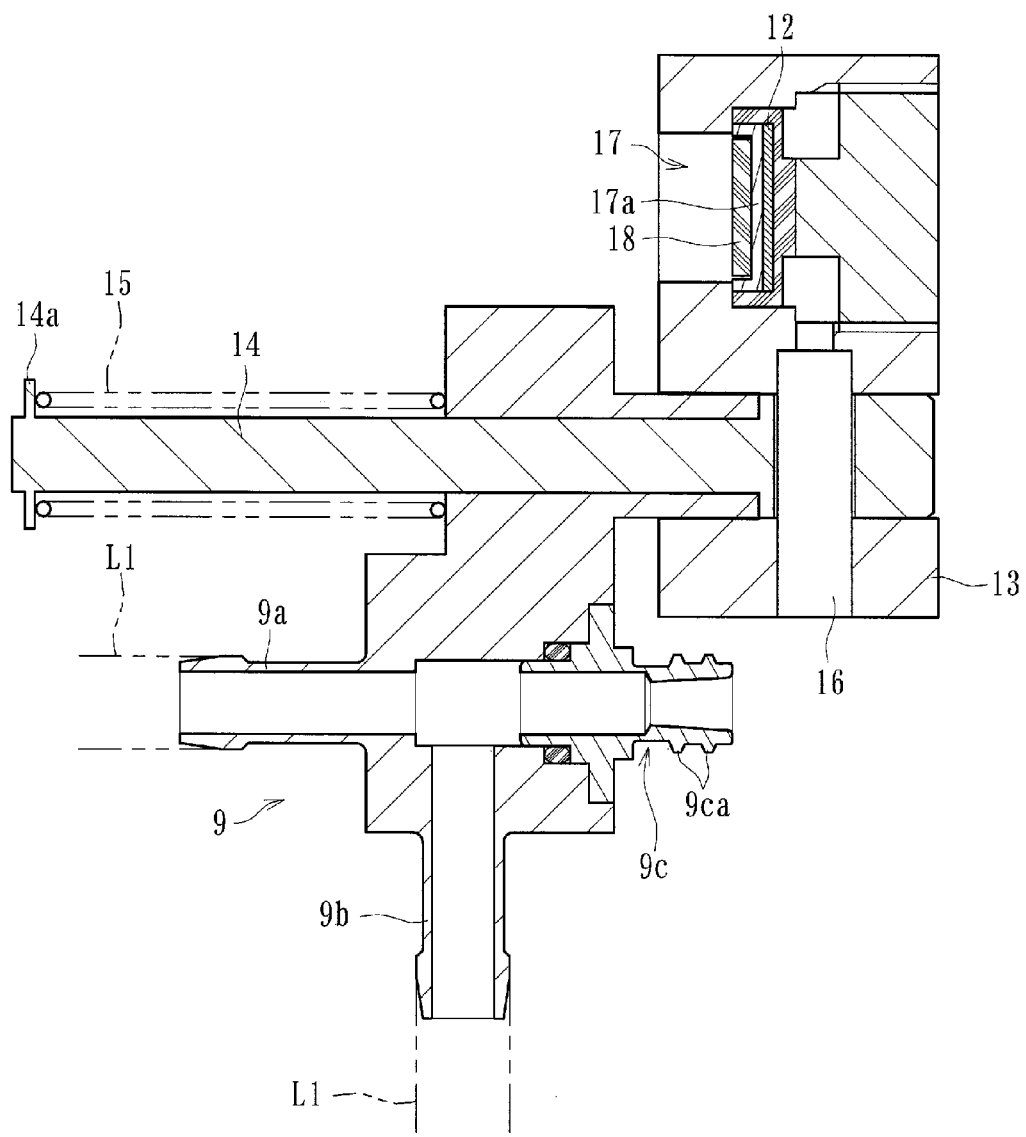
FIG. 7 is a schematic cross-sectional view illustrating a dialysate extraction device (state where the opening/closing device is detached) of the dialysate extraction apparatus.

Similar to the first embodiment, the dialysate extraction apparatus according to the present embodiment is connected to the dialysate introduction line L1 of the blood purification apparatus as illustrated in FIG. 1. As illustrated in FIGS. 5 to 7, the dialysate extraction apparatus includes the dialysate extraction device 9 that has the introduction port 9a and the discharge port 9b which are connected to the dialysate introduction line L1 (flow route of a liquid) and which can circulate the liquid (dialysate) and that has the collection port 9c which can collect the circulated liquid; a cap 17 serving as the opening/closing device which is attachable to and detachable from the collection port 9c of the dialysate extraction device 9 and which can open and close the collection port 9c : a sealing device 18; and the heating device 12.

The cap 17 according to the present embodiment is configured to have the sealing device 18 formed on one surface of an interposition member 17a and the heating device 12 formed on the other surface. The sealing device 18 is attached to the cap 17 and seals the collection port 9c in a state where the cap 17 is attached to the collection port 9c of the dialysate extraction device 9. In the present embodiment, the sealing device 18 is made of a rubber member. The sealing device 18 is adapted to have a plate-shaped sealing member, and can seal the collection port 9c by coming into close contact with a peripheral edge of the tip opening of the collection port 9c. It is preferable to form the interposition member 17a using a metallic material having excellent thermal conductivity. It is preferable to form members other than sealing device 18 and the interposition member 17a in the cap 17 using a resin material in order to keep thermal insulation.

If the heating device 12 is energized and heated, it is possible to heat the sealing device 18 via the interposition member 17a. The heat is transferred to the collection port 9c of the dialysate extraction device 9 via the sealing device 18, and thus, it is possible to heat a portion for sealing (in the present embodiment, an opening edge portion of the collection port 9c) of the collection port 9c. That is, the heating device 12 can heat and disinfect both of the sealing device 18 and the portion to be heated of the collection port 9c, respectively.

In the present embodiment, similar to the first embodiment, the apparatus is provided with the holding device 13 which holds the cap 17 and can switch between a state where the cap 17 is attached to the collection port 9c of the dialysate extraction device 9 (refer to FIG. 5) and a state where the cap 17 is detached from the collection port 9c (refer to FIG. 7). A configuration of the holding device 13 is the same as that of the first embodiment. In a state where the cap 17 covers the collection port 9c (refer to FIG. 5), the cap 17 is pressed against the collection port 9c by the biasing force of the spring 15, thereby holding a closed state.

In addition, if the holding device 13 together with the cap 17 is moved (moved in the rightward direction in FIG. 5) against the biasing force of the spring 15, the cap 17 is left in a state separated away from the collection port 9c, and the cap 17 is rotated about the center of the shaft member 14, it is possible to leave the collection port 9c in an opened state as illustrated in FIG. 7. In this manner, it is possible to connect the syringe or the connecting device such as the connecting line L3 to the collection port 9c.

According to the present embodiment, the apparatus is provided with the heating device 12 which can heat the sealing device 18 of the cap 17. Therefore, it is possible to automate the disinfecting work for the collection port 9c or the sealing device 18 of the cap 17. It is possible to reliably and easily clean the collection port 9c or the sealing device 18 of the cap 17. In addition, according to the present embodiment, the heating device 12 is fixed to the cap 17. Therefore, it is possible to heat and disinfect the sealing device 18 either in a state where the cap 17 is attached to the collection port 9c or in a state where the cap 17 is detached from the collection port 9c.

Further, according to the present embodiment, in a state where the cap 17 is attached to the collection port 9c of the dialysate extraction device 9, the heating device 12 can heat and disinfect the collection port 9c via the sealing device 18. Therefore, it is possible to reliably disinfect the collection port 9c in a closed state. Furthermore, the heating device 12 according to the present embodiment is adapted to have the semiconductor heater which can perform heating by means of energizing and can be held at the setting temperature. Therefore, it is possible to eliminate a need for a separate device such as a thermistor for keeping the temperature constant, and thus, it is possible to simplify a configuration of the apparatus.

In addition, the cap 17 is held by the holding device 13. Therefore, it is possible to firmly and reliably seal the collection port 9c by using the cap 17, and it is possible to avoid loss of the cap 17 when the collection port 9c is left in an opened state. In addition, if there is provided a detection device for detecting a direction of the holding device 13 (rotating position about the center of the shaft member 14), it is possible to detect whether the collection port 9c is in an opened state or in a closed state.

Next, a dialysate extraction apparatus according to a third embodiment of the present invention will be described.

Figure 8:
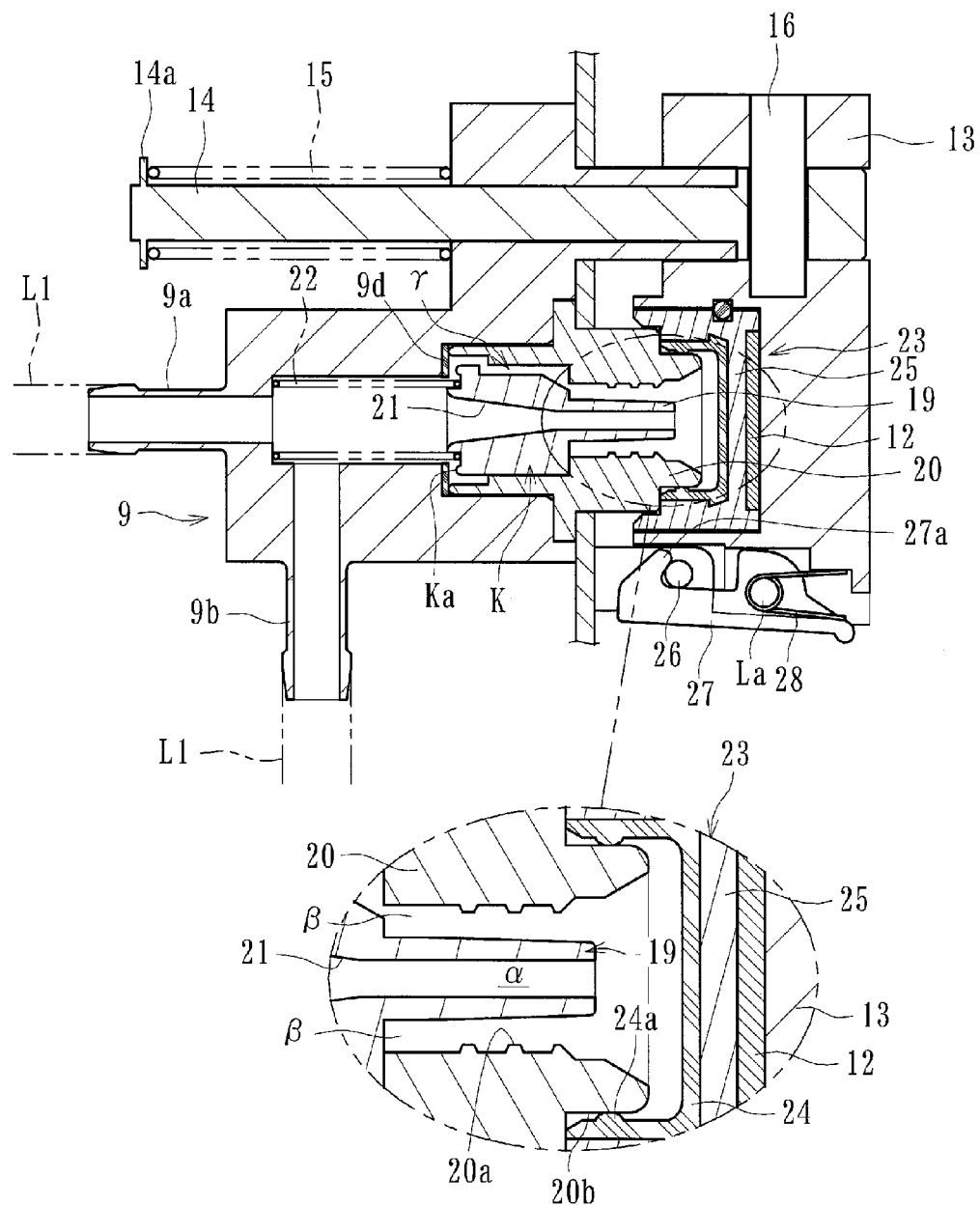
FIG. 8 is a schematic cross-sectional view illustrating a dialysate extraction apparatus (state where an opening/closing device is attached to a collection port) according to a third embodiment of the present invention.
Figure 9:
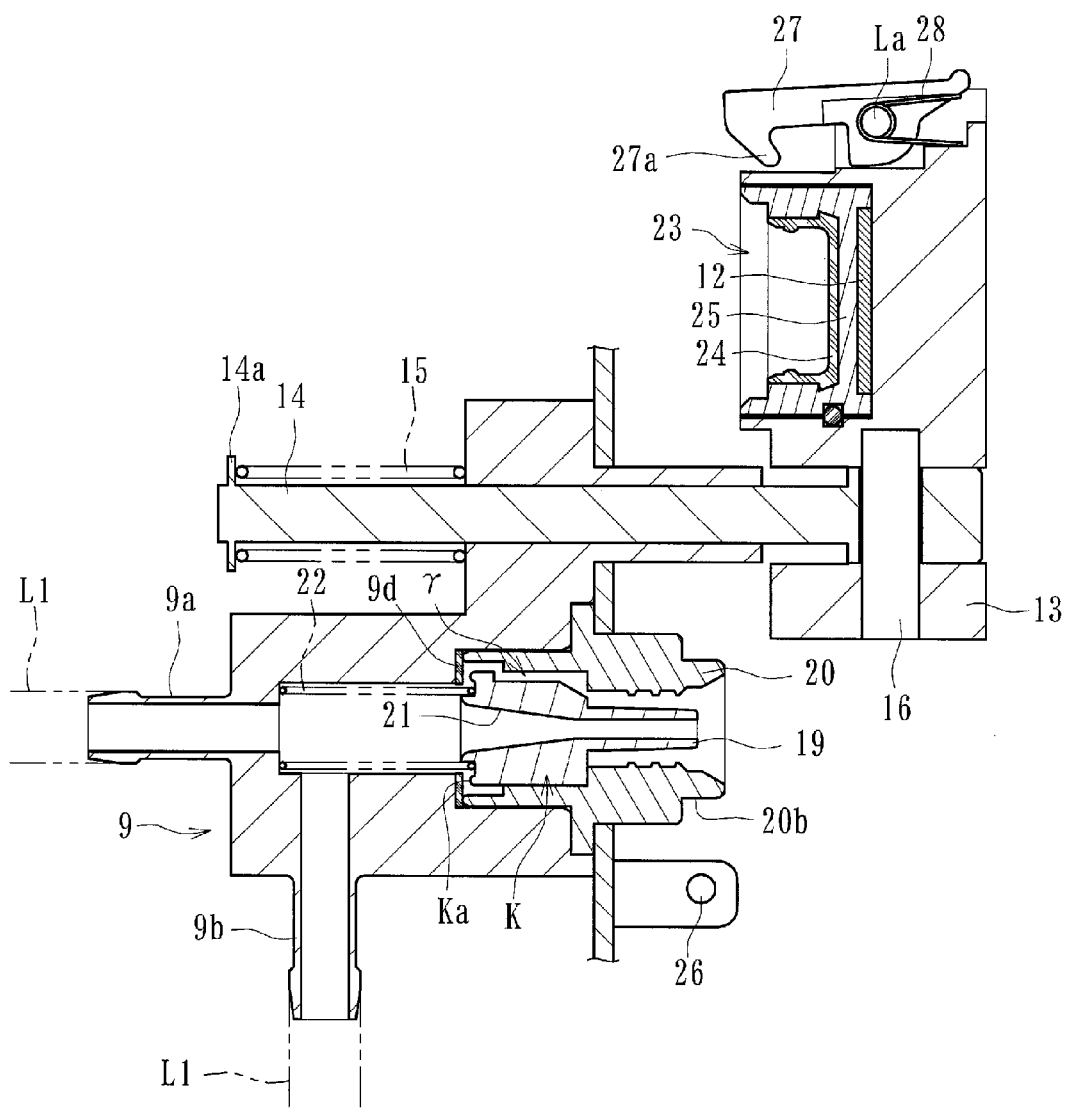
FIG. 9 is a schematic cross-sectional view illustrating a dialysate extraction device (state where the opening/closing device is detached) of the dialysate extraction apparatus.

Similar to the first and second embodiments, the dialysate extraction apparatus according to the present embodiment is connected to the dialysate introduction line L1 of the blood purification apparatus as illustrated in FIG. 1. As illustrated in FIGS. 8 to 9, the dialysate extraction apparatus includes the dialysate extraction device 9 that has the introduction port 9a and the discharge port 9b which are connected to the dialysate introduction line L1 (flow route of a liquid) and which can circulate the liquid (dialysate) and that has a collection port 19 which can collect the circulated liquid; a cap 23; a sealing device 24; and the heating device 12.

The dialysate extraction device 9 according to the present embodiment has a cylindrical outer peripheral wall 20 which covers an outer periphery of the collection port 19. An outer peripheral surface of the outer peripheral wall 20 has a portion for sealing 20b which can come into contact and be sealed with the sealing device 24 (specifically, a convex portion 24a of the sealing device 24) of the cap 23 (opening/closing device). An inner peripheral surface thereof has a screw portion 20a which can be screwed to a screw portion 29ba (refer to FIG. 10) of a connecting device 29 formed in the base end of the connecting line L3, respectively. That is, the collection port 19 can be connected to the connecting line L3 via the connecting device 29 by the connecting device 29 being locked and fixed to the outer peripheral wall 20.

The outer peripheral wall 20 according to the present embodiment configures a portion of the collection port 19, and is formed to protrude so as to cover a protruding end of the collection port 19. That is, a protruding dimension of the outer peripheral wall 20 is set to be larger than a protruding dimension of the collection port 19. Thus, the outer peripheral wall 20 is in a state of covering the protruding end of the collection port 19. In this manner, even in a state where the cap 23 is detached from the collection port 19, it is possible to prevent a person's finger from touching the collection port 19. Therefore, it is possible to more reliably perform hygiene management.

Figure 10:
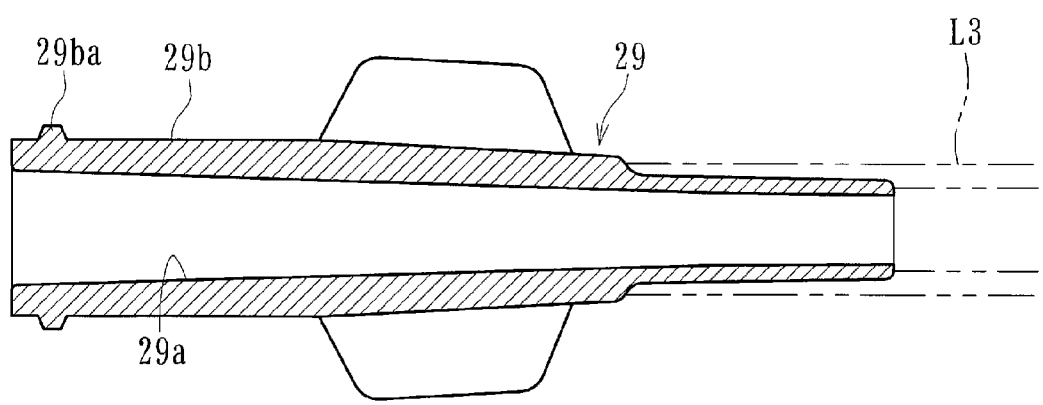
FIG. 10 is a schematic cross-sectional view illustrating a connecting device which can be connected to the collection port of the dialysate extraction apparatus.

In contrast, as illustrated in FIG. 10, the connecting device 29 is attached to a tip portion of the connecting line L3 for circulating the liquid collected through the collection port 19, and is adapted to have a substantially cylindrical-shaped member having an inner peripheral surface 29a and an outer peripheral surface 29b. The screw portion 29ba which can be screwed to the screw portion 20a of the outer peripheral wall 20 is formed integrally with a tip side (connecting portion side with respect to the collection port 19) of the outer peripheral surface 29b. The inner peripheral surface 29a of the connecting device 29 is fitted to the outer peripheral surface of the collection port 19, and the screw portion 29ba of the outer peripheral surface 29b of the connecting device 29 is screwed and locked to the screw portion 20a formed on the inner peripheral surface of the outer peripheral wall 20. In this manner, the connecting line L3 can be connected to the collection port 19.

As described above, the inner peripheral surface 29a of the connecting device 29 is fitted to the outer peripheral surface of the collection port 19 and the outer peripheral surface 29b of the connecting device 29 is locked to the inner peripheral surface of the outer peripheral wall 20, thereby enabling the connecting line L3 to be connected to the collection port 19. Thus, a connecting surface of the connecting device 29 with respect to the collection port 19 becomes the inner peripheral surface thereof (inside of the connecting device 29). Accordingly, it is possible to prevent a person's finger from touching the connecting surface thereof. Therefore, it is possible to more reliably perform hygiene management.

Here, in a state of the cap 23 being attached thereto, the collection port 19 of the dialysate extraction device 9 according to the present embodiment is configured to divide a guide route α which guides the liquid introduced from the introduction port 9a into the collection port 19, and a discharge route β which discharges the liquid guided by the guide route α to the discharge port 9b side. That is, if the cap 23 is attached to the outer peripheral wall 20, the sealing device 24 seals the protruding end surface side of the outer peripheral wall 20 so as to form a sealed space. The sealed space is divided into the guide route α and the discharge route β by the collection port 19. Thus, the inside of the collection port 19 becomes the guide route α and a section between the outer peripheral surface of the collection port 19 and the inner peripheral surface of the outer peripheral wall 20 becomes the discharge route β.

As described above, the collection port 19 according to the present embodiment has a function for collecting the liquid by using the connecting device 29 which is connected thereto, and in a state of the cap 23 being attached thereto, also has a function for dividing the guide route α and the discharge route β. In the present embodiment, the collection port 19 is configured to have the cylindrical-shaped member. However, any other shape (for example, a rectangular shape in cross section or the like) may be employed if a tubular member can divide the guide route α and the discharge route β.

In contrast, a connecting route γ for connecting the discharge route β and a flow route of the discharge port 9b side is formed in the dialysate extraction device 9. In this manner, the liquid flowing from the introduction port 9a to the tip of the collection port 19 via the guide route α is discharged from the discharge port 9b after passing through the discharge route β and the connecting route γ. Then, the liquid joins the liquid flowing from the introduction port 9a to the discharge port 9b and can be discharged from the discharge port 9b.

Furthermore, the dialysate extraction device 9 according to the present embodiment includes a pressure difference forming device 21 which increases a pressure of the liquid flowing to the guide route α more than a pressure of the liquid flowing to the discharge port 9b, out of the liquid introduced from the introduction port 9a. The pressure difference forming device 21 is adapted to include a circulation route of the liquid flowing from the introduction port 9a to the collection port 19. The circulation route has a tapered surface in which a diameter of the flow route is gradually decreased toward the collection port 19 side (right side in FIG. 8). In this manner, it is possible to increase the pressure of the liquid flowing from the introduction port 9a to the collection port 19 relative to the pressure of the liquid flowing from the introduction port 9a to the discharge port 9b.

In addition, the pressure difference forming device 21 and the collection port 19 according to the embodiment are adapted to have an integrated component K (for example, an integrally molded component). If the pressure difference forming device 21 and the collection port 19 are adapted to be the integrated component K in this way, it is possible to reduce the number of components in the dialysate extraction device 9, and thus, it is possible to reduce the manufacturing cost or the maintenance cost. The pressure difference forming device 21 and the collection port 19 may be individually formed and combined together so as to be the integrated component K.

Furthermore, in a peripheral edge of the base end side (left end side in FIGS. 8 and 9) in the integrated component K, a convex-shaped sealing portion Ka is formed. A member to be sealed 9d is arranged in a portion opposing the sealing portion Ka. In addition, the integrated component K is always biased by a spring 22 in a direction in which the sealing portion Ka is away from the member to be sealed 9d. Then, when the connecting device 29 is connected to the collection port 19 (that is, during a process when the screw portion 29ba of the connecting device 29 is screwed to the screw portion 20a formed on the inner peripheral surface of the outer peripheral wall 20), the integrated component K is moved against the biasing force of the spring 22, and the sealing portion Ka comes into contact with the member to be sealed 9d. In this manner, it is possible to block the connecting route γ.

In a state where the connecting device 29 is connected to the collection port 19, the liquid is blocked not to flow outward via the discharge route β. In a state where the connecting device 29 is connected to the collection port 19, the liquid is blocked not to flow outward via the discharge route β. Accordingly, when collecting the liquid from the collection port 19 via the connecting device 29, it is possible to reliably prevent the liquid from leaking outward through the discharge route β. Therefore, it is possible to more excellently circulate the collected liquid in the connecting line L3.

Incidentally, in the cap 23 according to the present embodiment, a cross section of an interposition member 25 is formed in a U-shape. The U-shaped sealing device 24 is formed along the inner peripheral surface of the interposition member 25, and the heating device 12 is fixed to a rear surface side of the interposition member 25. The sealing device 24 is attached to the cap 23, and seals the collection port 9c (in the present embodiment, seals a space including the collection port 9c) in a state where the cap 23 is attached to the collection port 19 of the dialysate extraction device 9 (in the present embodiment, a state where the cap 23 is attached to the outer peripheral wall 20). In the present embodiment, the sealing device 24 is made of a rubber material.

The sealing device 24 is adapted to have a sealing member whose cross section is a U-shape, and has a convex portion 24a formed inward in a convex shape. If the cap 23 is attached to the collection port 19 (outer peripheral wall 20), the convex portion 24a can come into contact with and seal the portion for sealing 20b of the outer peripheral wall 20. It is preferable to form the interposition member 25 using a metallic material with excellent thermal conductivity.

If the heating device 12 is energized and heated, it is possible to heat the sealing device 24 via the interposition member 25. The heat thereof is transferred to the outer peripheral surface of the outer peripheral wall 20 via the sealing device 24, and the portion for sealing 20b of the outer peripheral wall 20 (in the present embodiment, the outer peripheral surface of the outer peripheral wall 20) can be heated. That is, the heating device 12 can heat and disinfect both of the sealing device 24 and the portion for sealing 20b of the outer peripheral wall 20, respectively.

Similar to the first and second embodiments, the present embodiment is provided with the holding device 13 which holds the cap 23 and can switch between a state where the collection port 19 is closed by attaching the cap 23 to the outer peripheral wall 20 of the dialysate extraction device 9 (refer to FIG. 8) and a state where the collection port 19 is opened by detaching the cap 23 from the outer peripheral wall 20 (refer to FIG. 9). The configuration of the holding device 13 is the same as those in the first and second embodiments. In a state where the cap 23 covers the collection port 19 (refer to FIG. 8), the cap 23 is pressed against the collection port 19 by the biasing force of the spring 15, thereby holding a closed state.

In addition, if the holding device 13 together with the cap 23 is moved against the biasing force of the spring 15 (moved in the rightward direction in FIG. 9), the cap 23 is left in a state of being separated away from the collection port 19, and the cap 23 is rotated about the center of the shaft member 14, it is possible to leave the collection port 19 in an opened state as illustrated in FIG. 9. In this manner, it is possible to connect the syringe or the connecting device 29 such as the connecting line L3 to the collection port 19 (to be more exact, the outer peripheral wall 20).

Furthermore, the present embodiment is provided with a locking device 27 which can hold a closed state of the cap 23. The locking device 27, a tip of which has a locking claw 27a, can be freely oscillated about a center of an oscillation axle La, and the locking claw 27a is locked to a rod-shaped portion for locking 26 formed in a fixing side. In this manner, the closed state of the cap 23 can be held in the configuration. The locking device 27 is always biased by the spring 28 in a direction where the locking claw 27a is locked to the portion for locking 26.

In a state where the cap 23 covers the collection port 19 (refer to FIG. 8), the locking claw 27a is locked to the portion for locking 26, and the cap 23 is pressed against the outer peripheral wall 20 (collection port 19 side) by the biasing force of the spring 15, thereby holding the closed state. In addition, it is possible to release the locking of the locking claw 27a from the portion for locking 26 by oscillating the locking device 27 against the biasing force of the spring 28. Therefore, if the holding device 13 is rotated about the center of the shaft member 14, as illustrated in FIG. 9, it is possible to leave the collection port 19 in an opened state.

According to the present embodiment, the apparatus is provided with the heating device 12 which can heat the sealing device 24 of the cap 23. Therefore, it is possible to automate the disinfecting work for the outer peripheral wall 20 configuring the collection port 19 or the sealing device 24 of the cap 23. It is possible to reliably and easily clean the outer peripheral wall 20 or the sealing device 24 of the cap 23. In addition, according to the present embodiment, the heating device 12 is fixed to the cap 23. Therefore, it is possible to heat and disinfect the sealing device 24 either in a state where the cap 23 is attached to the collection port 19 (outer peripheral wall 20) or in a state where the cap 23 is detached from the collection port 19 (outer peripheral wall 20). Similar to the first and second embodiments, the heating device 12 according to the present embodiment is adapted to have the semiconductor heater which can perform heating by means of energizing and can be held at the setting temperature. Therefore, it is possible to eliminate a need for a separate device such as a thermistor for keeping the temperature constant, and thus, it is possible to simplify a configuration of the apparatus.

In addition, the cap 23 is held by the holding device 13. Therefore, it is possible to firmly and reliably seal the collection port 19 by using the cap 23. When the collection port 19 is left in an opened state, it is possible to avoid loss of the cap 23. In addition, if there is provided a detection device for detecting a direction of the holding device 13 (rotating position about the center of the shaft member 14), it is possible to detect whether the collection port 19 is in an opened state or in a closed state.

Next, a dialysate extraction apparatus according to a fourth embodiment of the present invention will be described.

Figure 11:
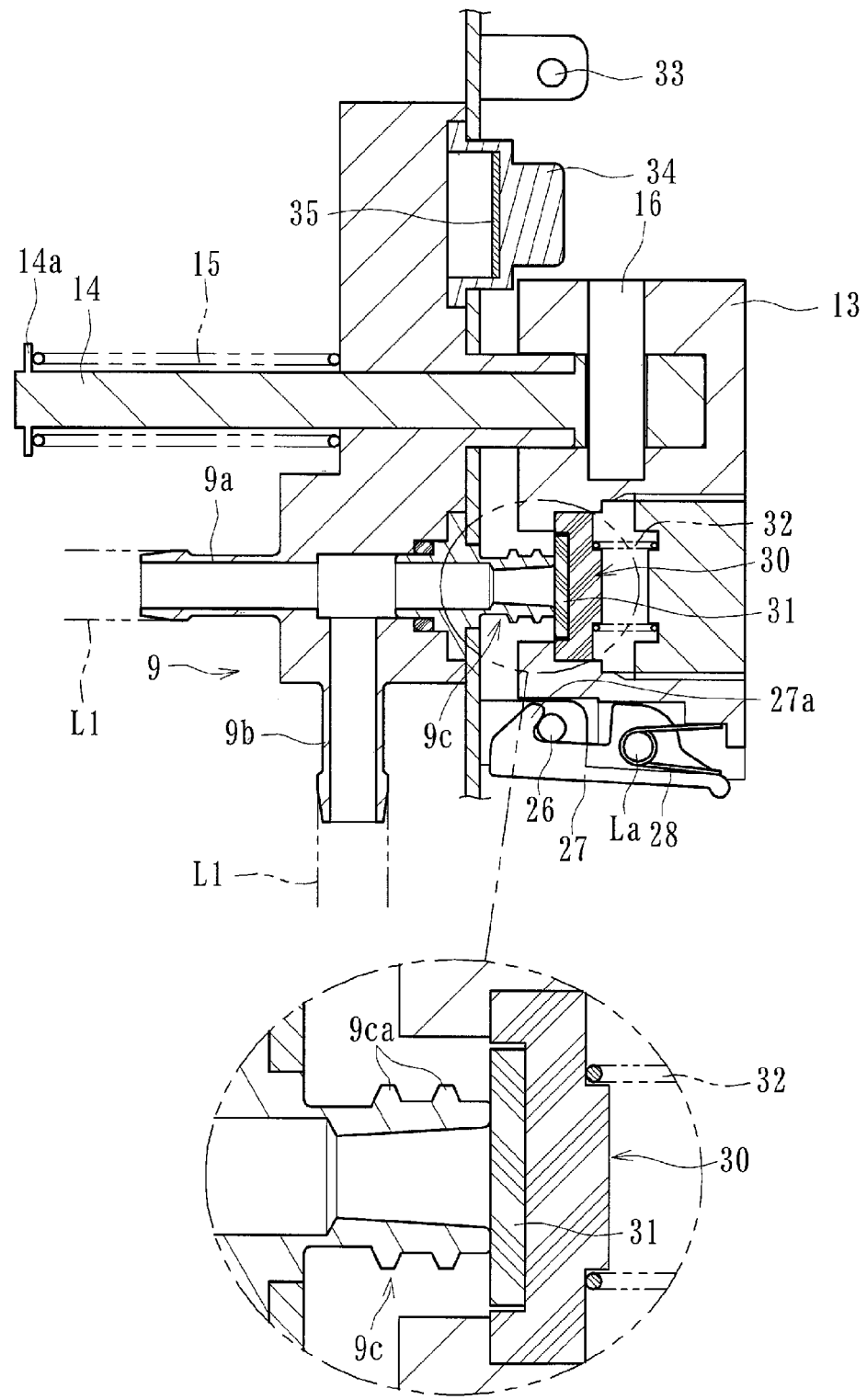
FIG. 11 is a schematic cross-sectional view illustrating a dialysate extraction apparatus (state where an opening/closing device is attached to a collection port) according to a fourth embodiment of the present invention.
Figure 12:
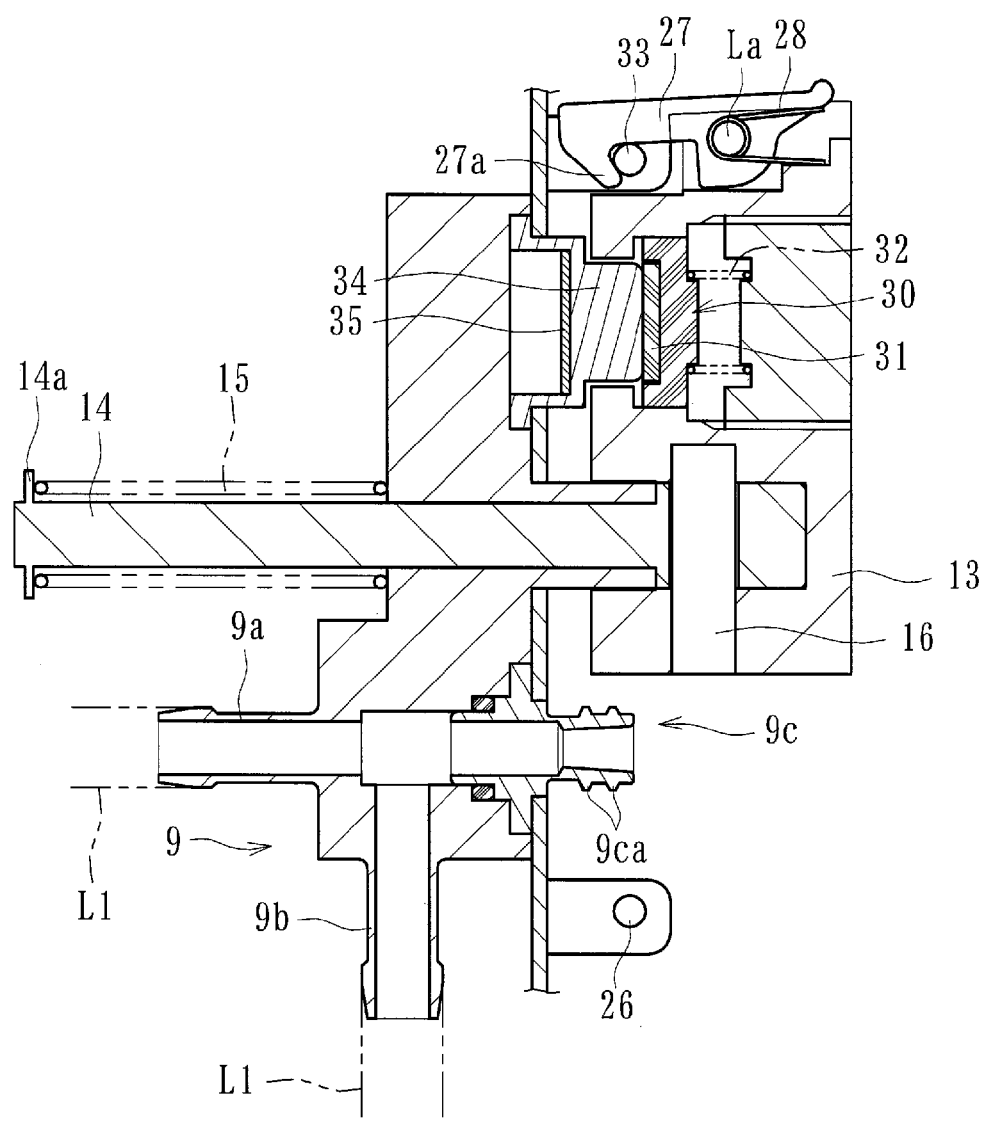
FIG. 12 is a schematic cross-sectional view illustrating a dialysate extraction device (state where the opening/closing device is detached and placed on a placement device) of the dialysate extraction apparatus.

Similar to the first to third embodiments, the dialysate extraction apparatus according to the present embodiment is connected to the dialysate introduction line L1 of the blood purification apparatus as illustrated in FIG. 1. As illustrated in FIGS. 11 and 12, the dialysate extraction apparatus includes the dialysate extraction device 9 that has the introduction port 9a and the discharge port 9b which are connected to the dialysate introduction line L1 (flow route of a liquid) and which can circulate the liquid (dialysate) and that has the collection port 9c which can collect the circulated liquid; a cap 30 as the opening/closing device which can be attached to or detached from the collection port 9c of the dialysate extraction device 9 and which can open and close the collection port 9c; a sealing device 31: a heating device 35; and a placement device 34.

The cap 30 according to the present embodiment is configured so that one surface has the sealing device 31 and the other surface is always biased by a spring 32 in the leftward direction in FIGS. 11 and 12. The sealing device 31 is attached to the cap 30 and seals the collection port 9c in a state where the cap 30 is attached to the collection port 9c of the dialysate extraction device 9. The sealing device 31 is adapted to have a plate-shaped sealing member, is biased by the spring 32, and can come into close contact with and seal a peripheral edge of the tip opening of the collection port 9c.

Here, as illustrated in FIG. 12, the present embodiment is provided with the placement device 34 which places the cap 30 detached from the collection port 9c of the dialysate extraction device 9. The heating device 35 is attached to the placement device 34. The placement device 34 is made of a metallic material having excellent thermal conductivity, and internally has a space for fixing the heating device 35.

The heating device 35 can heat the sealing device 31 of the cap 30 which is left in a state of being detached from the collection port 9c, and similar to the first to third embodiments, is adapted to have the semiconductor heater which can perform heating by means of energizing and can be held at the setting temperature. The heating device 35 is arranged in close contact with the inner peripheral surface in the internal space of the placement device 34. Therefore, the placement device 34 can be heated from the inside thereof.

If the heating device 35 is energized and heated, it is possible to heat the placement device 34. The heat thereof is transferred to the sealing device 31 of the cap 30 detached from the collection port 9c of the dialysate extraction device 9, and the sealing device 31 can be heated. That is, it is possible to heat and disinfect the sealing device 31 of the cap 30 via the placement device 34 by energizing the heating device 36 in a state where the cap 30 detached from the collection port 9c of the dialysate extraction device 9 is placed on the placement device 34.

Similar to the first to third embodiments, the present embodiment is provided with the holding device 13 which holds the cap 30 and can switch between a state where the collection port 9c is closed by attaching the cap 30 to the collection port 9c of the dialysate extraction device 9 (refer to FIG. 11) and a state where the collection port 9c is opened by detaching the cap 30 from the collection port 9c (refer to FIG. 12). The configuration of the holding device 13 is the same as those in the first to third embodiments. In a state where the cap 30 covers the collection port 9c (refer to FIG. 11), the cap 30 is pressed against the collection port 9c by the biasing force of the spring 15 and the spring 32, thereby holding a closed state.

In addition, if the holding device 13 together with the cap 30 is moved against the biasing force of the spring 15 (moved in the rightward direction in FIG. 12), the cap 30 is left in a state of being separated away from the collection port 9c, and the cap 30 is rotated about the center of the shaft member 14, it is possible to leave the collection port 9c in an opened state as illustrated in FIG. 12. In this manner, it is possible to connect the syringe or the connecting device such as the connecting line L3 to the collection port 9c.

Furthermore, the present embodiment is provided with the locking device 27 which can hold a closed state and an opened state of the cap 30. The locking device 27, the tip of which has the locking claw 27a, can be freely oscillated about the center of the oscillation axle La, and the locking claw 27a is locked to the rod-shaped portions for locking 26 and 33 formed in the fixing side. In this manner, the closed state or the opened state of the cap 30 can be held in the configuration. The locking device 27 is always biased by the spring 28 in the direction where the locking claw 27a is locked to the portions for locking 26 and 33.

In a state where the cap 30 covers the collection port 9c (refer to FIG. 11), the locking claw 27a is locked to the portion for locking 26, and the cap 30 is pressed against the collection port 9c side by the biasing force of the spring 15 and the spring 32, thereby holding the closed state. In addition, it is possible to release the locking of the locking claw 27a from the portion for locking 26 by oscillating the locking device 27 against the biasing force of the spring 28. Therefore, if the holding device 13 is rotated about the center of the shaft member 14, as illustrated in FIG. 12, it is possible to leave the collection port 9c in an opened state and to place the cap 30 on the placement device 34.

However, in the present embodiment, even in a state where the collection port 9c is opened, the locking claw 27a is locked to the portion for locking 33, and the cap 30 is pressed against the placement device 34 side by the biasing force of the spring 15 and the spring 32, thereby holding a placing state of the cap 30. Here, in the present embodiment, in addition to the spring 15, the cap 30 is biased against the placement device 34 side by the spring 32. Thus, it is possible to excellently bring the cap 30 into close contact with the placement device 34. Therefore, it is possible to more reliably heat and disinfect the sealing device 31 by using the heating device 35.

According to the present embodiment, the apparatus is provided with the heating device 35 which can heat the sealing device 31 of the cap 30 placed on the placement device 34. Therefore, it is possible to automate the disinfecting work for the sealing device 31 of the cap 30. It is possible to reliably and easily clean the sealing device 31 of the cap 30. In addition, according to the present embodiment, the apparatus is provided with the placement device 34 which places the cap 30 detached from the collection port 9c of the dialysate extraction device 9, and the heating device 35 is attached to the placement device 34. Therefore, it is possible to avoid loss of the cap 30 detached from the collection port 9c by using the placement device 34, and it is possible to achieve heat disinfection for the placed cap 30.

In particular, in the present embodiment, the cap 30 switched over to a state of being detached from the collection port 9c by the holding device 13 is configured to be placed on the placement device 34. Thus, it is possible to simultaneously carry out switching work using the holding device 13 and placement work on the placement device 34. Therefore, it is possible to improve workability, thereby enabling the cap 30 to be excellently heated and disinfected thereafter. Similar to the first to third embodiments, the heating device 35 according to the present embodiment is adapted to have the semiconductor heater which can perform heating by means of energizing and can be held at the setting temperature. Therefore, it is possible to eliminate a need for a separate device such as a thermistor for keeping the temperature constant, and thus, it is possible to simplify a configuration of the apparatus.

According to the first to fourth embodiments as described above, it is possible to provide the blood purification apparatus (hemodialysis apparatus) including the dialysate extraction apparatus which can automate the disinfecting work for the collection port or the sealing device of the cap (opening/closing device), and can reliably and easily clean the collection port or the sealing device of the cap (opening/closing device).

Hitherto, the present embodiments have been described, but the present invention is not limited thereto. For example, instead of the semiconductor heater, the heating device may be other generic heaters. In this case, it is preferable to separately arrange a thermistor in order to enable a heater to hold a constant heating temperature. In addition, any one of the present embodiments is configured so that the cap is held by the holding device 13. However, the cap may not be held by the holding device 13.

Further, the blood purification apparatus which adopts the present embodiments may have any other embodiment. For example, those which introduce the dialysate to a chamber or discharge the dialysate from the chamber may be used instead of the duplex pump 7, or those which include the blood purifier according to another embodiment instead of the dialyzer 1 may be used. Furthermore, in the present embodiments, any dialysate extraction apparatus is arranged in the dialysate introduction line L1 of the dialysis device, but may be arranged in other flow routes inside the dialysis device.

As long as there is provided a dialysate extraction apparatus including a heating device which can heat a sealing device of an opening/closing device, the dialysate extraction apparatus can be applied to those which have different outer shapes or other additional functions.

REFERENCE SIGN LIST 1. dialyzer (blood purifier)
2 arterial blood circuit
3 venous blood circuit
4 blood pump
5 arterial air trap chamber
6 venous air trap chamber
7 duplex pump
8 ultrafiltration pump 9 dialysate extraction device
10 cap (opening/closing device)
11 sealing device
12 heating device
13 holding device
14 shaft member
15 spring
16 shaft member
17 cap (opening/closing device)
18 sealing device
19 collection port
20 outer peripheral wall
21 pressure difference forming device
22 spring
23 cap (opening/closing device)
24 sealing device
25 interposition member
26 portion for locking
27 locking device
28 spring
29 connecting device
30 cap (opening/closing device)
31 sealing device
32 spring
33 portion for locking
34 placement device
35 heating device

The invention claimed is:

1. A dialysate extraction apparatus comprising:
a dialysate extraction device including:
an introduction port,
a discharge port, and
a collection port,
wherein a liquid extends through a flow route that extends from the introduction port to the discharge port which are connected by the flow route so that the flow route can circulate the liquid and the collection port is connected to the flow route so that the liquid can be collected from the flow route;
an opening/closing device that is attachable to and detachable from the collection port of the dialysate extraction device and can open and close the collection port;
a sealing device that is attached to the opening/closing device and seals the collection port in a state where the opening/closing device is attached to the collection port of the dialysate extraction device; and
a heating device that is attached to the opening/closing device and can heat the sealing device of the opening/closing device in a state where the opening/closing device is attached to the collection port and in a state where the opening/closing device is detached from the collection port.

2. The dialysate extraction apparatus according to claim 1, wherein the heating device can heat and disinfect the collection port via the sealing device in a state where the opening/closing device is attached to the collection port of the dialysate extraction device.

3. The dialysate extraction apparatus according to claim 1, further comprising:
a placement device that places the opening/closing device detached from the collection port of the dialysate extraction device,
wherein the heating device is attached to the placement device.

4. The dialysate extraction apparatus according to claim 3, further comprising:
a holding device that holds the opening/closing device and can switch between a state where the opening/closing device is attached to the collection port of the dialysate extraction device and a state where the opening/closing device is detached from the collection port.

5. The dialysate extraction apparatus according to claim 1, wherein the heating device includes a semiconductor heater which can perform heating by means of energizing and can be held at a setting temperature.

6. A apparatus comprising:
a blood purification apparatus containing the dialysate extraction apparatus according to claim 1.

7. The dialysate extraction apparatus according to claim 2, wherein the heating device includes a semiconductor heater which can perform heating by means of energizing and can be held at a setting temperature.

8. The dialysate extraction apparatus according to claim 4, wherein the holding device includes a first shaft member and a second shaft member and the holding device is rotatable about a center of the first shaft member so that the opening/closing device is rotatably moved away from and towards the collection port.

9. The dialysate extraction apparatus according to claim 8, wherein the holding device includes a spring that biases the opening/closing device so that when the opening/closing device is aligned with the collection port a biasing force of the spring moves the opening/closing device into communication with the collection port closing the collection port.

10. The dialysate extraction apparatus according to claim 1, wherein the heating device is heated to a setting temperature of 65° C. or higher.

11. The dialysate extraction apparatus according to claim 1, wherein the opening/closing device includes an interposition member made of a metallic material.

12. The dialysate extraction apparatus according to claim 1, wherein the heating device heats and disinfects the sealing device in a state where the opening/closing device is attached to the collection port and in a state where the opening/closing device is detached from the collection port.

13. The dialysate extraction apparatus according to claim 1, further comprising: a locking device which holds the opening and closing device a closed state and an opened state.

14. The dialysate extraction apparatus according to claim 11, wherein members of the opening/closing device other than the sealing device and the interposition member are made of a resin material.

15. The dialysate extraction apparatus according to claim 1, wherein the heating device includes a thermistor so that the heating device holds a constant heating temperature.

16. The dialysate extraction apparatus according to claim 1, further comprising:
a placement device made of a metallic material that places the opening/closing device detached from the collection port of the dialysate extraction device,
wherein the heating device is fixed to an internal space of the placement device.

17. The dialysate extraction apparatus according to claim 11, wherein the opening/closing device is configured so that the sealing device is on one surface of the interposition member and the heating device is on another surface.

18. The dialysate extraction apparatus according to claim 1,
wherein the collection port is positioned on a substantially identical straight line with respect to the introduction port.

19. The dialysate extraction apparatus according to claim 5,
wherein the energized heating device heats and disinfects the sealing device and a portion for sealing of the collection port.

20. The dialysate extraction apparatus according to claim 1, further comprising:
a placement device that places the opening/closing device detached from the collection port of the dialysate extraction device;
a holding device that holds the opening/closing device and can switch between a state where the opening/closing device is attached to the collection port of the dialysate extraction device and a state where the opening/closing device is detached from the collection port; and
wherein the heating device includes a semiconductor heater which can perform heating by means of energizing and can be held at a setting temperature and is located between the sealing device and the placement device and can heat and disinfect the collection port via the sealing device.

* * * * *